United States Patent [19]

Frey

[11] Patent Number: 5,085,626
[45] Date of Patent: Feb. 4, 1992

[54] PHYSIOTHERAPEUTIC APPARATUS PROVIDED FOR PRODUCING A MAGNETIC FIELD TO BE USED AS A THERAPEUTIC MEANS

[75] Inventor: Guy Frey, Bruxelles, Belgium

[73] Assignee: Alsthom International S.A., Brussels, Belgium

[21] Appl. No.: 446,334

[22] Filed: Dec. 5, 1989

[30] Foreign Application Priority Data

Dec. 6, 1988 [BE] Belgium .............................. 8801372

[51] Int. Cl.⁵ .............................................. A61N 2/02
[52] U.S. Cl. .......................................... 600/13; 600/15
[58] Field of Search .................................. 600/9-15; 335/219

[56] References Cited

U.S. PATENT DOCUMENTS

| | | | |
|---|---|---|---|
| 765,690 | 7/1904 | True | 600/13 |
| 1,216,183 | 2/1917 | Swingle | 600/13 |
| 3,337,776 | 6/1964 | Elmi | 600/13 |
| 3,963,959 | 6/1976 | Howell | 361/45 |
| 4,327,344 | 4/1982 | Luckenbach | 355/253 |
| 4,356,476 | 10/1982 | Cardone et al. | 335/295 |
| 4,674,482 | 6/1987 | Waltonen et al. | 600/14 |
| 4,850,959 | 7/1989 | Findl | 600/14 |
| 4,911,686 | 3/1990 | Thaler | 600/14 |

OTHER PUBLICATIONS

American Institute of Physics Handbook, pp. 5-160, (1982).

Primary Examiner—Francis Jaworski
Assistant Examiner—Scott R. Akers
Attorney, Agent, or Firm—Spencer & Frank

[57] ABSTRACT

An apparatus for physiotherapeutic treatment of cells and tissues in a living body by directly inducing the magnetic energy of a magnetic field into the body in order to cure or stimulate repair of the treated body part. The magnetic field is generated by an induction coil having a solenoid with a substantially linear core fixed therein. The coil has a length of at least twice the length of the core diameter. The apparatus further comprises an electric current generator for feeding the coil.

20 Claims, 2 Drawing Sheets

PHYSIOTHERAPEUTIC APPARATUS PROVIDED FOR PRODUCING A MAGNETIC FIELD TO BE USED AS A THERAPEUTIC MEANS

BACKGROUND OF THE INVENTION

The invention relates to a physiotherapeutic apparatus comprising an electrical current generator and a coil connected to the current generator, the coil comprising a solenoid and a core fixed inside the solenoid and provided for generating a magnetic field to be used as therapeutic means.

Such an apparatus is known and used for treating diseases by means of a magnetic field. The electric current supplied by the generator is sent to the coil in order to create a magnetic field. In the known apparatuses either a flat coil is introduced into a small plate which is put on the body to be treated or the coil has a large diameter and the body to be treated is introduced within the surrounding formed by the solenoid.

In order to treat a large variety of diseases it is absolutely necessary to create, by means of the apparatus, a magnetic field of which the field lines are of good quality and which apparatus enables the magnetic filed to reach, in a precise manner, a well-determined place or point situated inside the body to be treated. That point can even be relatively deep in the body to be treated.

A drawback of the known apparatus is that there is not obtained a magnetic field of which the fieldlines are of sufficient quality in order to treat a large variety of diseases.

SUMMARY OF THE INVENTION

It is an object of the invention to provides a physiotherapeutic apparatus which is able to produce a magnetic field of which the field lines are concentrated in the axis of the core and of which the dispersion is reduced.

Therefore a physiotherapeutic apparatus according to the invention is characterized in that said core has a length which is at least twice the one of the core diameter. That coil configuration enables to generate a magnetic field having a high homogenity degree inside the coil and enables a concentration of the field lines within the coil axis, and thus to reduce the field lines dispersion.

A first preferred embodiment of an apparatus according to the invention is characterized in that the solenoid has at least 1,000 windings. This enables one to generate a magnetic field of sufficient intensity for treating a large number of diseases.

A second preferred embodiment of an apparatus according to the invention is characterized in that the core is a steel core having a carbon content less than or equal to 0.40%. This enables one to obtain a good relative magnetic permeability of the core, while having a reduced core dimension.

Preferably the core is made of a material having a relative magnetic permeability less than 1200. This ensures limiting the size of the magnetic field and thus the field lines dispersion.

Preferably an area situated around the central core axis is made of a material having a relative magnetic permeability higher than the one of the material used for the area situated around the core wall. This enables to reduce the field lines dispersion.

A third preferred embodiment of an apparatus according to the invention is characterized in that the core is made of cold drawn mild steel. Cold drawn mild steel is particularly suitable for use as core and enables a quick saturation of the field lines.

A fourth preferred embodiment of an apparatus according to the invention is characterized in that the electric current generator comprises an alternative current generator provided for generating an alternating current, the intensity and/or the frequency of which is variable. This enables one to treat a first category of diseases.

A fifth preferred embodiment of an apparatus according to the invention is characterized in that the electric current generator is provided for generating a pulsed current, the frequency and/or the intensity of which is variable. This enables to treat another category of diseases.

Preferably the apparatus comprises a polarity selector. This enables an inversion of the polarity of the magnetic field without having to modify the position of the coil.

Preferably the coil is held in a box of plastic material provided with at least a belt and fixed with the belt to a band, the belt being mounted on said box in such a manner as to enable the box to rotate with respect to the belt. The band enables one to place and fix easily the coil to the body to be treated. The fact that the box can rotate with respect to the belt enables one to invert the position of the coil and thus to invert the polarity of the magnetic field.

The invention will be described in more detail by means of the example shown in the drawing. It will be clear that the invention is in no way limited to the described example and that within the scope of the invention several alternatives are possible.

DESCRIPTION OF THE PREFERRED EMBODIMENTS

Figure 1:
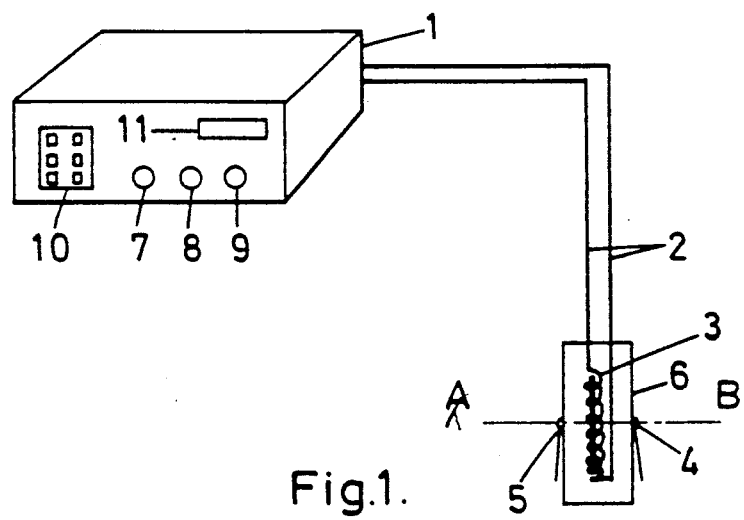
FIG. 1 shows an overall view of a preferred embodiment of a physiotherapeutic apparatus according to the invention.
Figure 7:
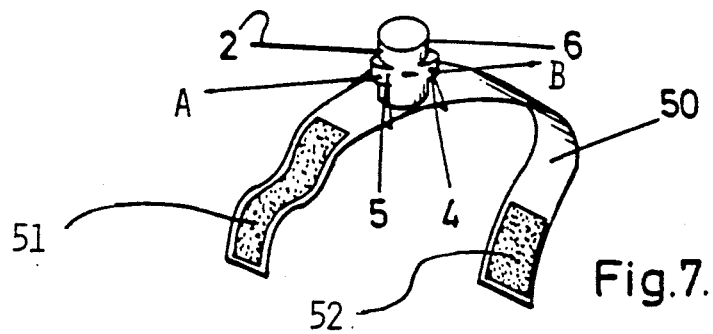
FIG. 7 illustrates a core held in a box fixed to a band.

The physiotherapeutic apparatus illustrated in FIG. 1 comprises an electric current generator an output of which being connected by means of a conductor wire 2 to a coil 3. The coil is held in a box 6, for example, a nylon box or a box made of another rigid and isolating plastic material. The box is preferably provided with two belts 4 and 5 which are fixed to a band 50, such as illustrated in FIG. 7, and enabling one to fix the box and the coil around a part of a body to be treated. The band is preferably provided with adhesive means 51, 52 enabling one to fix the band around said part of said body. Preferably the belt 4 and 5 are mobile, enabling the box to rotate around the axis AB and thus to modify the polarity direction of the magnetic field created by the coil when the latter is fed by a current supplied by generator 1.

In another embodiment, the physiotherapeutic apparatus according to the invention is provided for feeding several coils thus enabling one to apply a magnetic field at several points of the body to be treated. Further by using several coils, each held in a box and fixed by one or more bands, and also due to the fact that they are able to rotate, it is possible to apply in one point a south polarised magnetic field and in another point a north polarised magnetic field.

The current generator 1 is provided for generating either a direct current, or an alternating current, the intensity of which is variable. The generator 1 is also provided with means for modifying the frequency of the current. The selection of those different possibilities is realized by means of controls 7, 8 and 9 even as by means of a control keyboard 10. A display device 11, for example formed by an assembly of LED's, enables to display the value of the current even as of other information as for example the frequency, the polarity, etc.

Figure 2:
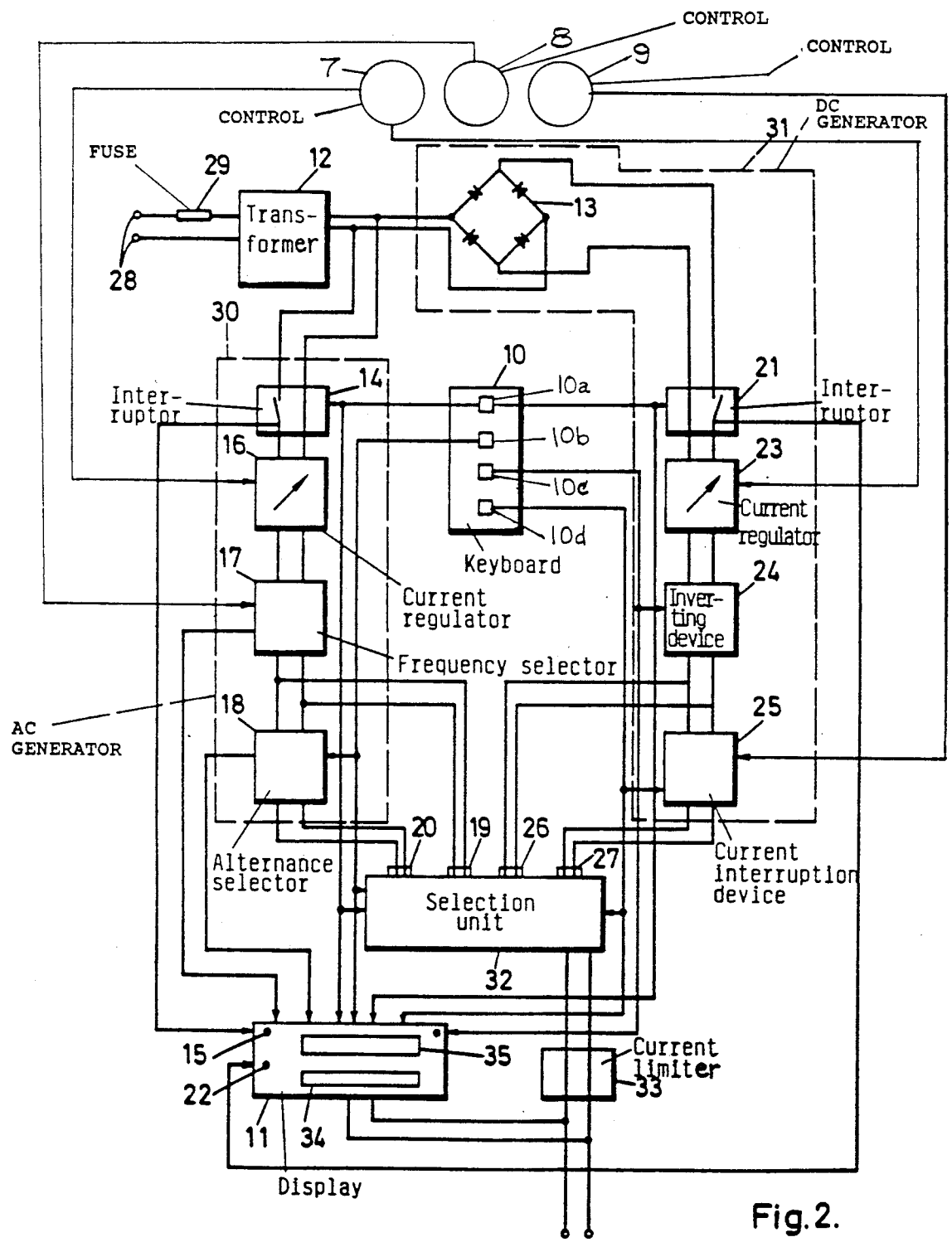
FIG. 2 illustrates, by means of a block schematic the main elements of a current generator to be used in an apparatus according to the invention.

FIG. 2 illustrates by means of a block schematic the main elements of a current generator being part of an apparatus according to the invention. The generator comprises an input 28 at which a feeding tension or voltage is applied, for example 220 Volts supplied by the main power lines. That tension is supplied to a transformer 12 which enables to transform a primary tension of for example 220 Volts into one or several secondary tension values, for example 9 Volts and/or 12 Volts. In order to limit the current supplied by the generator, a fuse 29, for example a 2-Ampere fuse, is mounted in the current supply line.

The output of the transformer 12 is connected on the one hand to an alternating current generator 30 and, on the other hand, to a direct current generator 31. The alternating current generator 30 comprises an interruptor 14, which is for example controlled by a key 10a of the keyboard 10, and which interruptor 14 enables switching the generator 30 on. The interruptor 14 is connected to a first light indicator 15, for example formed by a LED of the display 11, which first light indicator is switched on when the generator 30 is switched on. An output of the switch 14 is connected to a current regulator 16, for example formed by a variable resistance device. The regulator is positionable (as indicated by the arrow) by means of a control 7, thus enabling one to vary the intensity of the supplied current. An output of the regulator 16 is connected to an input of the frequency selector 17 which is controlled by means of a control 8. The frequency selector 17 enables one to choose the alternating current frequency supplied to the coil and thus to choose the frequency of the magnetic field created by the coil 1. The frequency selector 17 is connected to the display 11, thus enabling the display of the chosen frequency. Preferably the frequency is continuously variable within a 1 to 100 Hz-range.

An output of the frequency selector 17 is connected on the one hand to a first input 19 of a selection unit 32 and, on the other hand, to an input of an alternance selector 18 an output of which being connected to a second input 20 of the selection unit 32. The alternance selector 18 enables, when it is switched on one, to select one or the other alternances (half period) of the electric current wave and thus to obtain a north or south pulsed magnetic field, depending on having either chosen the one or the other half period. The alternance selector 18 is also connected to the display 11 enabling to display which one of the two half periods has been chosen. The indication of the choice of a half period and the switch on of the selection unit are for example realized by means of one or two keys (10b) of the keyboard 10.

The direct current generator 31 comprises a diode bridge rectifier 13, transforming an alternating current supplied at the output of the transformator 12 into a direct current. An output of the diode bridge rectifier 13 is connected to a second interrupter 21, which is for example also controlled by the key 10a of the keyboard 10, and which enables to switch on the direct current generator. The key 10a of the keyboard is provided in such a manner as to disable that the direct current generator is switched on when the alternative current is switched on, for example by using a selector for key 10a. The interruptor 21 is connected to a LED 22 of the display which, when it is switched on, indicates that the direct current generator is switched on.

An output of the interruptor 21 is connected to a current regulator 23, for example a variable resistance device. The regulator 23 is positionable by means of a control 7, thus enabling one to vary the intensity of the supplied current. An output of the regulator 23 is connected to an inverting device 24, which enables one to select the polarity of the current and thus of the magnetic field. The inverting device 24 is connected to a key 10c of the keyboard which thus enables one to position the inverting device 24 and thus to modify the polarity of the current. The key 10c is also connected to the display 11 in order to display, for example by means of a sign + or −, the chosen polarity. An output of the inverting device 24 is, on the one hand, connected to a third input 26 of the selection unit 32 and, on the other hand, to an input of a current interruption device 25. A control input of the device 25 is connected to the control 9. The interruption device 25 is provided with means, for example formed by an RC circuit and a transistor, enabling one to interrupt the current during time periods, of which the duration is variable, and thus to obtain a rectangular shaped wave. The manipulation of control 9 enables one to vary the duration of the time period and thus the frequency of the rectangular wave. The frequency can thus for example by varied between 1 and 100 Hz. An output of the device 25 is connected to a fourth input 27 of the selection unit 32. The key 10d of the keyboard is connected to another control input of the device 25 and enables one to switch on the device 25. The key 10d is also connected to the display device 11 thus displaying that the device 25 is switched on.

The selection unit 32 comprises first and second control inputs. The first control input is connected to key 10a which controls the interrupter 14 and the second control input is connected to key 10b which controls the alternance selector 18. A third control input of the selection unit 32 is connected to key 10d which controls the device 25. As a function of the choice indicated by means of the keyboard 10, the selection unit 32 selects a signal present on one of the four inputs 19, 20, 26 and 27 and transmits it at its output, which is connected by means of a current limitator 33 to the coil 3 (not shown in FIG. 2).

When by means of the key 10a the direct current generator 31 respectively the alternative current generator 30 has been chosen, LED 22 respectively 15 will be switched on and the selected unit 32 will connect one of the inputs 26, 27 respectively one of the inputs 19, 20 with its output. The choice between the inputs 19, 20 respectively the inputs 26, 27 is realized in function of the key 10b respectively 10c. When the alternance selector 18, respectively, the device 25 is switched on, the input 20, respectively, 27 will be connected to the output.

An output of the current limitator 33 is also connected to the display device 11 thus enabling to display on a screen 34 the current provides intensity supplied to the coil. The screen 35 enables a display of the current frequency, such as produced by the frequency selector 17 or the device 25.

The current limiter 33 serves, as its name indicates, to limit the current (for example to a maximum of 200 mA) crossing the coil and thus protects the coil.

It will be clear that within the scope of the invention several other embodiments for generator 1 are possible. Thus in another embodiment generator 1 does not comprise a selection unit 32 but comprises, for example, four individual outputs on which each time the coil can be switched on. In the latter case, the keys 10a, b and d are no longer necessary. The generator can also comprise several outputs for connecting several coils.

The electric current produced by the generator 1 is supplied to the coil 3 in order to create a magnetic field which will then be used as a therapeutic means. That use of therapeutic purposes imposes particular constraints to the magnetic field created by the coil and thus to the coil itself. Thus the magnetic field lines must sometimes be able to penetrate up to a distance of 40 cm within the human or animal body to be treated. Moreover, the magnetic field lines have, preferably, to be concentrated within the coil axis and have a reduced dispersion. Indeed, by magneto-therapy it is important to be able to apply a magnetic field at a well defined point of the body to be treated, and sometimes there must be avoided that a magnetic field is applied to neighbouring parts of the point to be treated. Particularly, for accupunture applications that constraint is of major importance. Care must thus be taken to create a magnetic field having a high quality and having field lines of a great purity. Moreover, it is necessary in order to treat certain diseases, such as diseases of a bony origin, for example, osteomyelites, to create magnetic fields having a magnetic intensity of at least 7,500 Gauss. On the other hand, for treating other types of more superficial diseases, such as for example diseases of tissular pathology, an intensity of 1000 Gauss is necessary or a pulsed magnetic field is necessary such as is, for example, the case when treating inflamatory diseases or ulcers. The intensity of the magnetic field required for acting against a lesion is essentially a function of the depth at which the lesion to be treated is situated. All those different constraints impose strict norms to the construction of the coil.

In order to create a magnetic field able to efficiently treat a large variety of diseases, the coil being part of a physiotherapeutic apparatus according to the invention satisfies the particular constraints which will be described in detail hereunder.

Figure 3:
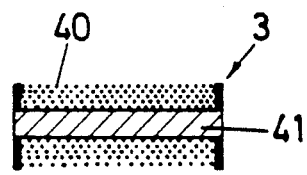
FIG. 3 shows a cross-section of a coil according to the invention.

FIG. 3 shows a cross-sectional view of a coil 3 according to the invention. The solenoid 40 comprises at least 1000 windings, but preferably 2000 windings of a wire, particularly a copper wire having, for example, a 0.25 mm diameter. In order to increase the relative magnetic permeability ($\mu_R$) of the coil and thus the magnetic intensity and the flux of the created magnetic field, the coil comprises a core 41 fixed inside the solenoid. Preferably, the coil has a circular cross-section.

In order to obtain a magnetic field satisfying the desired constraints, it is important that the coil has a length of at least twice the core diameter. Preferably, the coil length is nearly four times that of the core diameter. For example, when the core formed by a cylinder, comprises a diameter of 10 mm, it comprises a length of 30 mm which corresponds to the one of the coil, since preferably the core extends over the whole length of the coil. The choice of the coil dimension enables concentration of the magnetic field lines in the core axis and thus create a magnetic field having a considerable homogenity.

The homogeneity of the magnetic field is further improved by using a steel core having a carbon content less than or equal to 0.40% but preferably less than or equal than 0.25%. The use of such a steel enables a heavier concentration of the field of lines which thus are quickly in a saturated state in the core. That phenomenon provides a field lines spectrum which is very dense and which can reach a point situated at nearly 40 cm from the coil center.

To obtain such a core, it is necessary to submit the steel to a treatment. That treatment consists of letting the core quickly come up at a temperature of a maximum 600° C., followed by a very weak hammer-hardening during the cool-down period of the coil. During the hammer-hardening operation the core steel is submitted to a hammering enabling the steel to be more flexible and thus to reduce practically to zero the Foucault currents which could be induced into the core, when an electric current crosses through the solenoid. There is thus obtained that only very weak current losses occur into the coil causing only a very weak heating during the operation. In such a manner energy losses are also avoided and consequently this enables to maintain the magnetic field for a longer time.

As material forming the core, it is also possible to use cold-drawn iron (for example iron calibrated ST37), or polished iron. The choice of materials for the core is governed by the fact that preferably the relative magnetic permeability is less then 1,200. Indeed, in order to limit the dispersion of the field lines and the transmitted energy (energy which is too great could cause damage to the body to be treated) it is important that the magnetic field does not exceed an intensity of for example 10,000 Gauss inside the body to be treated.

Figure 4:
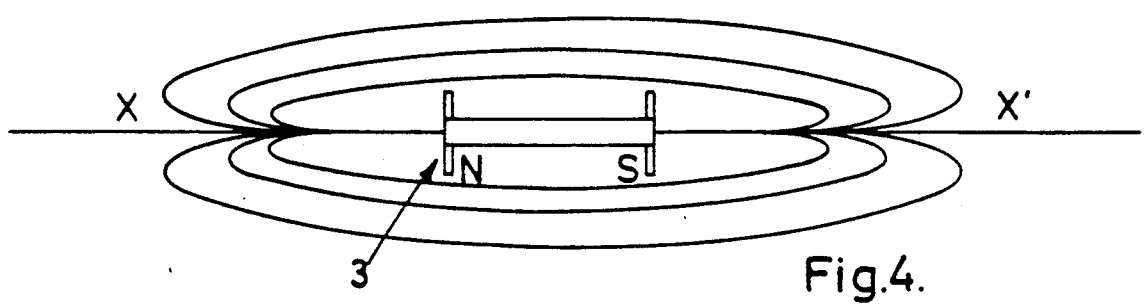
FIG. 4 illustrates the field lines of a magnetic field created by means of an apparatus according to the invention.

FIG. 4 illustrates the field lines of a magnetic field created by means of an apparatus according to the invention. As can be seen from FIG. 4, the field lines are concentrated within the core axis XX' and only show a weak dispersion thus enabling one to focus the magnetic field at a well defined point of the body to be treated.

Figure 5:
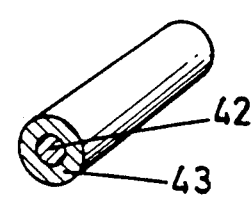
FIG. 5 illustrates a first type of a core to be used in a coil according to the invention.

FIG. 5 illustrates another embodiment of a core to be used in a coil according to the invention. The core has its inner core or center 42 made of another quality of steel than that used for the surrounding wall or layer of the core. For example the surrounding wall is produced in a harder steel than the steel used for the core center. The surrounding wall is, for example, produced in a polished steel while the center is made of a cold-drawn steel. It is thus achieved that the relative magnetic permeability in a zone situated around the central axis of the core is superior to the one situated in the area around the core wall.

Figure 6:
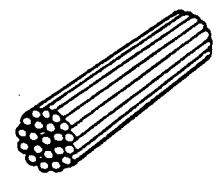
FIG. 6 illustrates a second type of a core to be used in a coil according to the invention.

FIG. 6 illustrates another embodiment of a core to be used in a coil according to the invention. The core is formed by an assembly of welding rods in copperized steel, for example, of the type G-y 41 (ISO 636/G232 Norm). The rods are, for example, assembled so as to form a cylinder having, for example, a 10 mm-diameter of 10 mm and a 38 mm-length.

The Table given hereunder shows by way of example certain values of the magnetic field created by an apparatus according to the invention. The values are obtained by using a 38 mm length coil with 2,000 windings and a 10 mm diameter core made of mild steel and having a relative magnetic permeability of for example 500.

| Amperage in mA | Magnetic induction in Gauss measured at the core center |
| --- | --- |
| 10 | 3.925 |
| 30 | 11.775 |
| 50 | 19.625 |
| 70 | 27.475 |
| 90 | 35.325 |
| 110 | 43.175 |
| 130 | 51.025 |
| 150 | 58.875 |
| 170 | 66.725 |
| 200 | 78.500 |

Thanks to the various possibilities for generator 1, it is possible to create by means of the coil several types of magnetic fields. Thus by opting for direct current (key 10a) one can create static magnetic fields, the intensity of which can, for example, vary (control 7) between 0 and 10,000 Gauss. The static magnetic fields are used when the therapeute desires to obtain an antalgic action or a restorative effect on the autonomic nervous system. The key 10c makes it possible to invert the polarity of the current and thus the polarity of the the magnetic field without it being necessary to invert the orientation of the coil. Indeed when the north pole is in contact with the body to be treated, a decontracting effect is obtained which diminished the muscular tonus, which is vaso-dilatory and cholineric with an anti-stress predominance. On the other hand, when the south pole is in contact with the treated body, a contraction effect is obtained which increases the muscular tonus. The magnetic fields originating from the south pole of the coil provoke vaso-constriction phenomena which oppose to inflammation vaso-dilatory processes.

The interruption device 25 enables one to obtain a pulsed north or south magnetic field according to the indicated polarity on key 10c.

One can thus obtain a pulsed magnetic field starting from the alternative current generator 30. Some examples of therapeutic treatment using pulsed magnetic fields are given hereunder.

| Frequencies between 1 and 10 Hz | Antalgic effects<br>Vasodilatation<br>Increase or decrease of the muscular tonus<br>Recommended frequencies: 2.6 Hz. |
| --- | --- |
| Frequencies between 11 and 20 Hz | Anti-inflammatory<br>Anti-oedematic<br>Recommended frequencies: 12, 13, 14 Hz. |
| Frequencies between 40 and 110 Hz | Frequencies ranging between 40 and 110 Hz are used for actions on the viscera. Recommended frequencies are situated between 42 and 55 Hz. They stimulate leucocytes. Action on the cells (ionic pump). Cicatrizing action. |
| | Ulcer treatments. |

By switching on (key 10b) the alternance selector 18, one can obtain a pulsed north or south magnetic field as a function of the operator's choice.

What is claimed is:

1. A physiotherapeutic apparatus comprising
    means for generating a concentrated magnetic field to be directly induced for therapeutic purposes into a living body to be treated, said magnetic field generating means including an induction coil having a solenoid and a substantially straight core fixed inside said solenoid, said coil having a length at least twice the diameter of the core, the magnetic field having poles located, respectively, at opposite ends of the core;
    an electric current generator connected to said induction coil; and
    means for orienting said coil to selectively place either one of said poles of the magnetic field in direct contact with the body to be treated.

2. An apparatus as claimed in claim 1, wherein said solenoid comprises at least 1,000 windings.

3. An apparatus as claimed in claim 1, wherein said core comprises a steel core having a carbon content of at most 0.40%.

4. An apparatus as claimed in claim 1, wherein said core comprises a material having a relative magnetic permeability less than 1,200.

5. An apparatus as claimed in claim 1, wherein said core comprises an inner core and an outer surrounding layer, said inner core comprises a first material, said outer surrounding layer comprises a second material, said first material having a relative magnetic permeability higher than the relative magnetic permeability of said second material.

6. An apparatus as claimed in claim 1, wherein said core comprises a cold-drawn mild steel or a copperized steel.

7. An apparatus as claimed in claim 1, wherein said core comprises an assembly of copperized steel rods.

8. An apparatus as claimed in claim 1, wherein said means for orienting said coil comprises a plastic box which encloses said induction coil.

9. An apparatus as claimed in claim 1, wherein said electric current generator comprises an alternating current generator for generating an alternating current, said electric current generator having means for varying one of the frequency and the intensity of the current.

10. An apparatus as claimed in claim 1, wherein said electric current generator comprises a direct current generator for generating a direct current, said electric current generator having means for varying the intensity of the current.

11. An apparatus as claimed in claim 1, wherein said electric current generator includes means for generating a pulsed current and for varying the frequency of the current.

12. An apparatus as claimed in claim 1, wherein said electric current generator includes a polarity selector.

13. An apparatus as claimed in claim 1, wherein said solenoid has a length of about 32 mm and comprises approximately 2,000 windings, each said winding having a diameter of about 0.25 mm, said core having a length of about 38 mm and having a diameter of about 10 mm.

14. An apparatus as claimed in claim 13, wherein said means for orienting said coil comprises a plastic box which encloses said induction coil, a band attaching said plastic box to a body to be treated, and a belt attached to said plastic box and to said band for enabling said plastic box to rotate with respect to said belt.

15. An apparatus as claimed in claim 1, wherein said means for orienting said coil comprises a plastic box which encloses said induction coil, a band attaching said plastic box to a body to be treated, and a belt attached to said plastic box and to said band for enabling said plastic box to rotate with respect to said belt.

16. An apparatus as claimed in claim 1, wherein said electric current generator includes means for generating a pulsed current and for varying the frequency and intensity of the current.

17. An induction coil for use in a physiotherapeutic apparatus having means for generating a concentrated magnetic field, said coil comprising a solenoid and a substantially straight core fixed inside said solenoid, said coil having a diameter and a length which is at least twice the core diameter; the magnetic field having poles located, respectively, at opposite ends of said core; and means for orienting said coil to selectively place either one of said poles of the magnetic field in direct contact with the body to be treated.

18. An induction coil as claimed in claim 17, wherein said solenoid has a length of about 32 mm and comprises approximately 2,000 windings, each said winding having a diameter of about 0.25 mm, said core having a length of about 38 mm and having a diameter of about 10 mm.

19. An induction coil as claimed in claim 18, wherein said means for orienting said coil comprises a plastic box which encloses said induction coil, a band attaching said plastic box to a body to be treated, and a belt attached to said plastic box and to said band for enabling said plastic box to rotate with respect to said belt.

20. An induction coil as claimed in claim 17, wherein said means for orienting said coil comprises a plastic box which encloses said induction coil, a band attaching said plastic box to a body to be treated, and a belt attached to said plastic box and to said band for enabling said plastic box to rotate with respect to said belt.

* * * * *